(12) United States Patent
Narayanan et al.

(10) Patent No.: US 6,306,285 B1
(45) Date of Patent: Oct. 23, 2001

(54) TECHNIQUES FOR SENSING METHANOL CONCENTRATION IN AQUEOUS ENVIRONMENTS

(75) Inventors: Sekharipuram R. Narayanan, Altadena; William Chun, Los Angeles; Thomas I. Valdez, Pasadena, all of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/056,054

(22) Filed: Apr. 6, 1998

Related U.S. Application Data

(60) Provisional application No. 60/041,872, filed on Apr. 8, 1997.

(51) Int. Cl.[7] .................................................. G01N 27/406
(52) U.S. Cl. ...................... 205/787; 205/783.5; 204/421; 204/422
(58) Field of Search ............................... 205/783.5, 787; 204/422, 421, 423, 424, 408

(56) References Cited

U.S. PATENT DOCUMENTS

| | | |
|---|---|---|
| 3,410,780 | 11/1968 | Holden . |
| 3,464,008 | 8/1969 | Meysson et al. . |
| 3,480,520 | 11/1969 | Smith . |
| 4,003,705 | 1/1977 | Buzza et al. . |
| 4,025,412 | 5/1977 | La Conti . |
| 4,575,410 | 3/1986 | Neti . |
| 4,629,664 * | 12/1986 | Tsukui et al. ........................... 429/23 |
| 4,744,954 * | 5/1988 | Campbell et al. ..................... 422/98 |
| 4,752,361 * | 6/1988 | Gautschi ............................... 205/784 |
| 4,875,900 * | 10/1989 | Kodachi et al. ...................... 204/408 |
| 5,118,398 | 6/1992 | Mc Elroy et al. . |
| 5,151,166 * | 9/1992 | Harral et al. ......................... 205/784 |
| 5,173,166 | 12/1992 | Tomantschger et al. . |
| 5,322,602 | 6/1994 | Razaq . |
| 5,518,830 * | 5/1996 | Worrel et al. ........................ 204/421 |
| 5,599,638 | 2/1997 | Surampudi et al. . |
| 5,773,162 * | 6/1998 | Surampudi et al. ................... 429/39 |
| 5,897,766 * | 4/1999 | Kawatsu ................................ 204/426 |

\* cited by examiner

*Primary Examiner*—Robert J. Warden, Sr.
*Assistant Examiner*—Kaj K. Olsen
(74) *Attorney, Agent, or Firm*—Fish & Richardson P.C.

(57) ABSTRACT

An analyte concentration sensor that is capable of fast and reliable sensing of analyte concentration in aqueous environments with high concentrations of the analyte. Preferably, the present invention is a methanol concentration sensor device coupled to a fuel metering control system for use in a liquid direct-feed fuel cell.

31 Claims, 8 Drawing Sheets

TECHNIQUES FOR SENSING METHANOL CONCENTRATION IN AQUEOUS ENVIRONMENTS

This application claims benefit under 35 USC 119(e) of the U.S. Provisional Application Ser. No. 60/041,872, filed on Apr. 8, 1997, the entirety of which is incorporated herewith by reference.

ORIGIN OF INVENTION

The invention described herein was made in the performance of work under a NASA contract, and is subject to the provisions of Public Law 96-517 (35 USC 202) in which the Contractor has elected to retain title.

FIELD

This disclosure generally relates to analyte concentration sensors and in particular fuel concentration sensors for use with a liquid direct-feed fuel cell.

BACKGROUND

The liquid direct-feed fuel cell is a device that generates electrical energy from the oxidation of organic fuels. Jet Propulsion Laboratory "JPL" developed a liquid direct-feed fuel cell using a solid-state electrolyte, preferably a solid polymer cation exchange electrolyte membrane. The subject matter of this implementation is described in U.S. Pat. No. 5,599,638, U.S. patent application Ser. No. 08/569,452 (Patent Pending), and U.S. patent application Ser. No. 08/827,319 (Patent Pending) the disclosures of which are incorporated by reference to the extent necessary for proper understanding.

FIG. 1 illustrates a typical structure of a JPL fuel cell with an anode 110, a solid electrolyte membrane 120, and a cathode 130. An anode 110 is formed on a first surface 140 of the solid electrolyte membrane 120 with a first catalyst for electro-oxidation. A cathode 130 is formed on a second surface 145 thereof opposing the first surface 140 with a second catalyst for electro-reduction. The anode 110, the solid electrolyte membrane 120, and the cathode 130 are hot press bonded to form a single multi-layer composite structure, referred to herein as a membrane electrode assembly "MEA" 150. An electrical load 160 is connected to the anode 110 and the cathode 130 for electrical power output.

A fuel pump 170 is provided for pumping an organic fuel and water solution into an anode chamber 180. The organic fuel and water mixture is withdrawn through an outlet port 190 and is re-circulated. Carbon dioxide formed in the anode chamber 180 is vented through a port 1100 within tank 1120. An oxygen or air compressor 1130 is provided to feed oxygen or air into a cathode chamber 1140.

Prior to use, the anode chamber 180 is filled with the organic fuel and water mixture. The cathode chamber 1140 is filled with air or oxygen either at ambient pressure or in a pressurized state. During operation, the organic fuel in the anode chamber 180 is circulated past the anode 110. Oxygen or air is pumped into the cathode chamber 1140 and circulated past the cathode 130. When an electrical load 160 is connected between the anode 110 and the cathode 130, electro-oxidation of the organic fuel occurs at the anode 110 and electro-reduction of oxygen occurs at the cathode 130. Electrons generated by electro-oxidation at the anode 110 are conducted through the external load 160 and are captured at the cathode 130. Hydrogen ions or protons generated at the anode 110 are transported directly across the solid electrolyte membrane 120 to the cathode 130. Thus, a flow of current is sustained by a flow of ions through the cell and electrons through the external load 160.

During operation, a fuel and water mixture in the concentration range of 0.5–3.0 mole/liter is circulated past the anode 110 within anode chamber 180. Preferably, flow rates in the range of 10–500 ml/min are used. As the fuel and water mixture circulates past the anode 110, the following electro-chemical reaction, for an exemplary methanol cell, occurs releasing electrons:

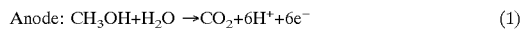

$$\text{Anode: } CH_3OH + H_2O \rightarrow CO_2 + 6H^+ + 6e^- \tag{1}$$

Carbon dioxide produced by the above reaction is withdrawn along with the fuel and water solution through outlet 190 and separated from the solution in a gas-liquid separator. The fuel and water solution is then re-circulated into the cell by pump 170.

Simultaneous with the electrochemical reaction described in equation (1) above, another electrochemical reaction involving the electro-reduction of oxygen, which captures electrons, occurs at the cathode 130 and is given by:

$$\text{Cathode: } O_2 + 4H^+ + 4e^- \rightarrow 2H_2O \tag{2}$$

The individual electrode reactions described by equations (1) and (2) result in an overall reaction for the exemplary methanol fuel cell given by:

$$\text{Cell: } CH_3OH + 1.5O_2 \rightarrow CO_2 + 2H_2O \tag{3}$$

During operation of the fuel cell, methanol is consumed at the anode 110. In order to maintain steady operation of the fuel cell system, the methanol concentration in the anode compartment 180 should be maintained. The concentration of methanol in the compartment can be sensed so that an appropriate amount of methanol is metered. The rate in which methanol is added to the system should be related to the rate of depletion of methanol in the system. Therefore, an accurate measure of fuel concentration is desirable for a fuel cell system.

SUMMARY

The inventors disclose an analyte concentration sensor that is capable of fast and reliable sensing of analyte concentration in aqueous environments with high concentrations of the analyte. Preferably, the present invention is a fuel concentration sensor device coupled to a fuel metering control system for use in a liquid direct-feed fuel cell. The present invention performs reliably in aqueous environments in the analyte concentration range 0.01 M–5 M and the temperature range 0–100 degrees Celsius.

The concentration sensor device includes a sensor element connected to a sensor response circuit. A reference element can be incorporated in several ways. One mode features a reference element coupled to both the sensor element and to the fuel metering control system. A preferred reference element for this mode is a thermocouple placed within the analyte fuel bath of the sensor element.

Another mode features a second sensor element as a reference element. This second sensor element is connected to the first sensor element; both the first and second sensor elements are connected to the sensor response circuit. In this mode, the concentration sensor device has a sensor element, a reference element, and a sensor response circuit.

The sensor element has a membrane electrode assembly mounted on supports. This sensor element resembles the fuel cell structurally. Like the fuel cell, the sensor element is fabricated by forming two catalyzed electrodes sandwiching a solid electrolyte membrane. The anode is preferably coated with platinum-ruthenium catalyst; the cathode is coated with platinum catalyst. Other catalyst formulations are possible.

However, the sensor element is operated quite differently from the standard fuel cell. The sensor element is connected to a sensor response circuit. This sensor response circuit provides a means to detect a concentration-dependent response from the sensor element.

In the preferred embodiment, both the anode and the cathode of the sensor element are immersed in a fuel bath. The anode is connected to the positive terminal of a constant voltage power supply or "potentiostat" and the cathode is connected to the negative terminal. The current flows through the sensor element causing electrochemical reactions to occur. This current is measured by an ammeter or a current measuring circuit connected in series in the path of the sensor response circuit, e.g. in series with the sensor element and the power supply.

At a certain high anode potential threshold, the current passing through the sensor cell becomes sensitive to the concentration of the fuel. This is because the mass transport of the fuel to the surface of the electrode becomes the current-limiting mechanism. This means that higher concentrations of methanol can sustain higher current densities. Therefore, the concentration sensor operates on the principle of the electrochemical oxidation of the fuel under mass transport limited conditions.

As discussed above, the current measured by the ammeter or the current measuring circuit represents the sensor response. The ammeter is connected to a fuel metering control system. The control system translates the ammeter output into a fuel concentration, e.g. using a pre-stored mathematical relation, or using a look up table. The fuel concentration verses measured current relationship may be highly temperature dependent. A reference element can be used to compensate the temperature dependence.

The preferred embodiments are suitable for online monitoring and control. Other advantages include large dynamic range of operation, easy standardization, relatively fast response time, and easy fabrication. Preferred modes of implementation are disclosed for use in concentration monitoring of fuels in liquid direct-feed fuel cells. However, applications of the present invention to other systems are also envisioned. These application systems include environmental monitoring, fuel manufacturing, and medical/biochemical detection devices.

BRIEF DESCRIPTION OF THE DRAWING

The objects and advantages of the present invention will become more readily apparent after reviewing the following detailed description and accompanying drawings, wherein.

DESCRIPTION OF THE PREFERRED EMBODIMENTS SENSOR ELEMENT FABRICATION

Figure 1:
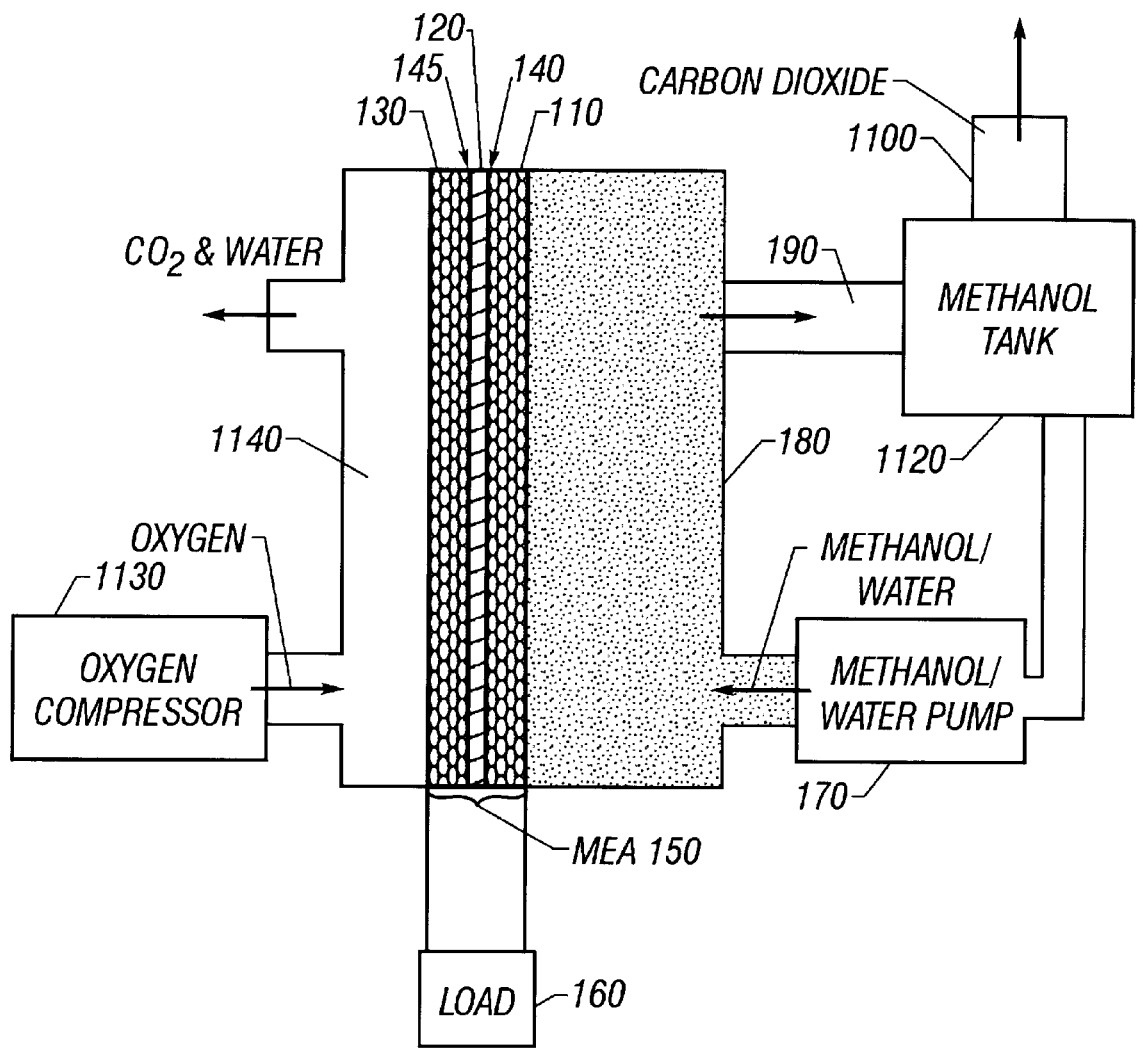
FIG. 1 illustrates a liquid direct-feed fuel cell.
Figure 2:
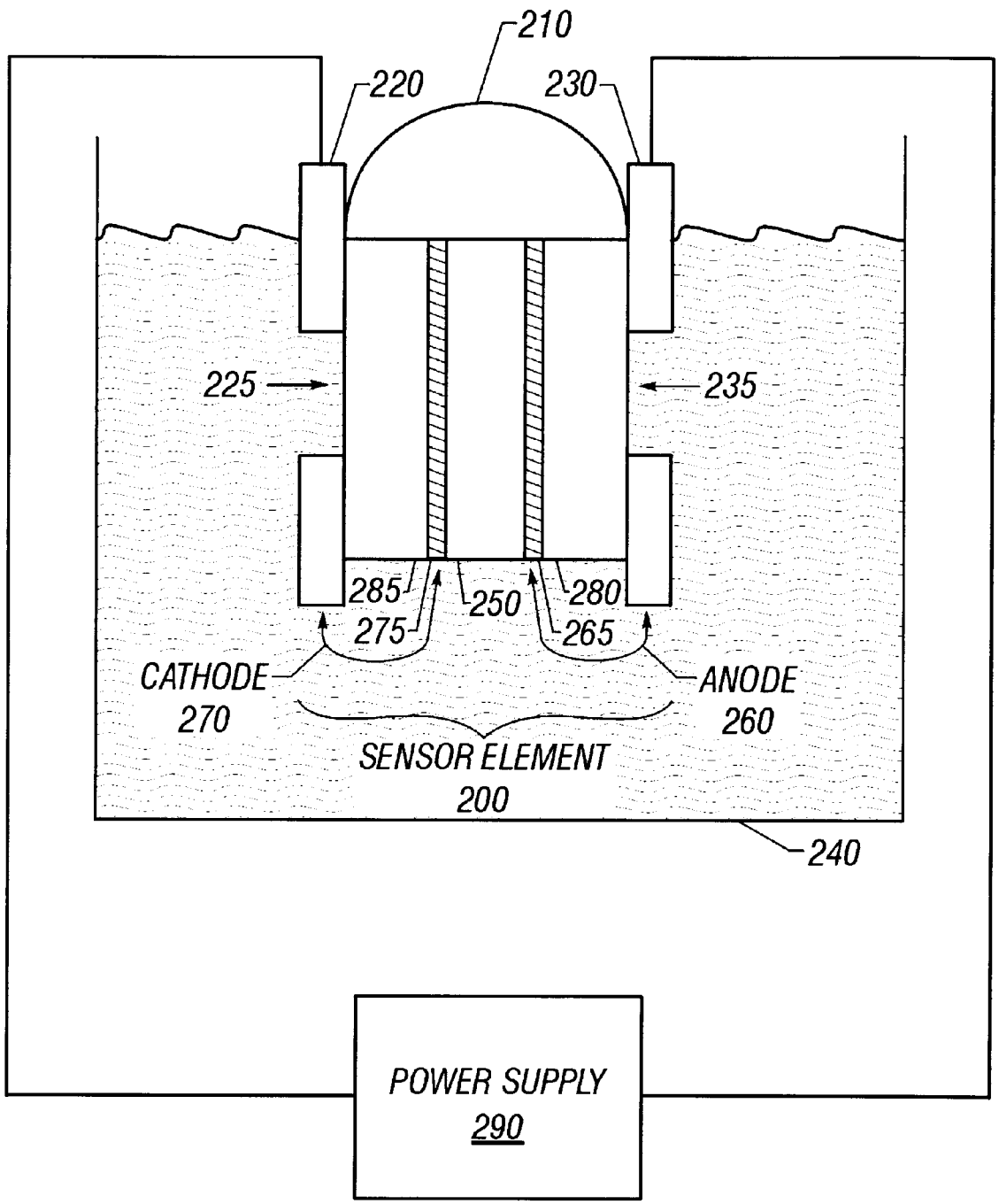
FIG. 2 is a schematic of sensor element construction.

A sensor element 200 is made by mounting a membrane electrode assembly 210 between two current collection plates 220,230, as shown in FIG. 2. The current collection plate 220 has a wide circular opening 225. The current collection plate 230 has a wide circular opening 235 to expose the sensor element 200 to the fuel solution 240. The plates 220, 230 serve as a mechanical support for the sensor element 200 and also acts as a current collector. Preferably, these plates 220, 230 are made of graphite. Other materials such as graphite-bonded resins, conductive or metallized plastics, coated-metals, e.g. titanium with platinum, gold or titanium nitride, noble metal coated stainless steel, such as stainless steel-coated with gold or platinum, can also be used.

Several membrane electrode assembly fabrication methods exist. The membrane electrode assembly can be fabricated using methods disclosed in U.S. Pat. No. 5,599,638, U.S. patent application Ser. No. 08/569,452, now U.S. Pat. No. 5,773,162, and U.S. patent application Ser. No. 08/827,319, now U.S. Pat. No. 5,945,231, the disclosure of which is incorporated herein by reference.

A solid electrolyte membrane 250, preferably made of NAFION™, is pre-treated in a swelling agent such as isopropanol. A catalyst ink including a preferred catalyst material, a wetting agent such as polytetrafluroethylene, e.g. TEFLON™, and an ionomer, e.g. NAFION™, can be directly applied to the solid electrolyte membrane 250. The membrane 250 is preferably coated with a platinum-ruthenium catalyst ink layer 265 on the anode 260 side and a platinum catalyst ink layer 275 on the cathode 270 side. Two sheets of porous electrode backing substrate 280, 285, preferably porous carbon paper, are pressed onto the coated membrane 250, one on either side, forming a membrane electrode assembly 210.

In an alternate technique, the catalyst ink is coated onto the electrode backing substrate 280, 285 instead of the membrane 250. The composite layer of anode backing substrate 280, solid electrolyte membrane 250, and cathode backing substrate 285 is hot press bonded to form the membrane electrode assembly 210.

The sensor element 200 having a membrane electrode assembly 210 mounted between two current collection plates 220, 230, is placed in a fuel solution 240 bath. Both the anode 260 and the cathode 270 are in contact with the fuel solution 240. The anode 260 and the cathode 270 are connected to a power supply 290. When the concentration sensor device is under current, the anode 260 reacts directly with methanol to form carbon dioxide and the cathode 270 reacts with the protons to form hydrogen. Since the cathode 270 is maintained within fluid 240, the cathode 270 does not react with air, and hence the protons do not react to form water as in the basic fuel cell reaction.

The sensor element reactions, include:

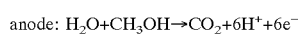

anode: $H_2O + CH_3OH \rightarrow CO_2 + 6H^+ + 6e^-$

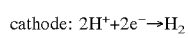

cathode: $2H^+ + 2e^- \rightarrow H_2$

Figure 3:
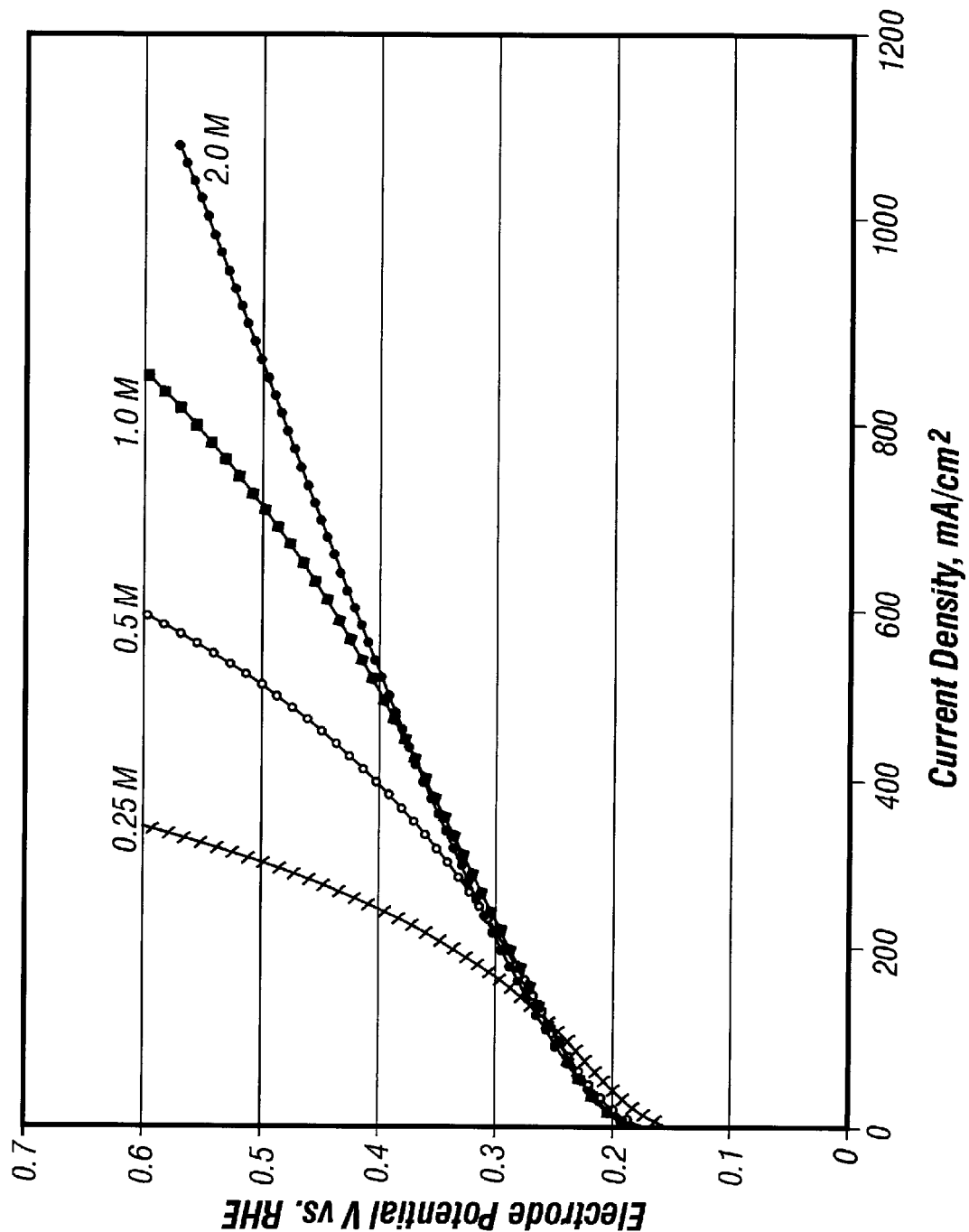
FIG. 3 is a graph illustrating the dependence of current density on applied potential during concentration sensor operation.

Initially, the current through the system is a function of the applied voltage as shown in FIG. 3. However, after a threshold high anode potential, in this experiment, above 0.3

V, the current passing through the sensor cell becomes sensitive to the concentration of methanol. This is because the mass transport of methanol to the surface of the anode becomes the current-limiting mechanism, and therefore higher concentrations of methanol can sustain higher current densities. The mass-transfer controlled current is an indicator of the concentration of methanol. This current hence represents the sensor response and is hence indicative.

Single Sensor Element Implementation

Figure 4A:
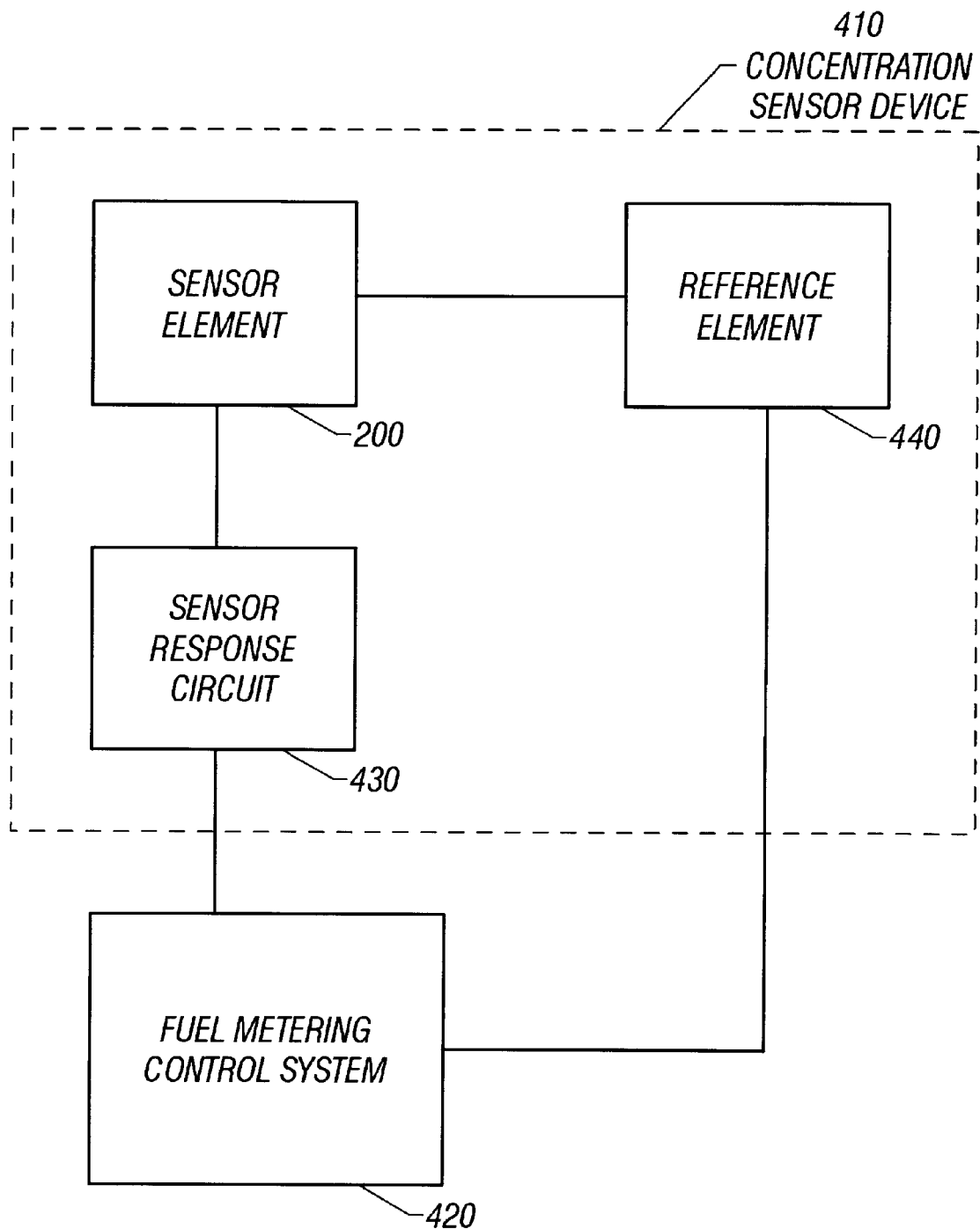
FIG. 4A is a block diagram illustrating a single sensor element implementation of the concentration sensor device.
Figure 4B:
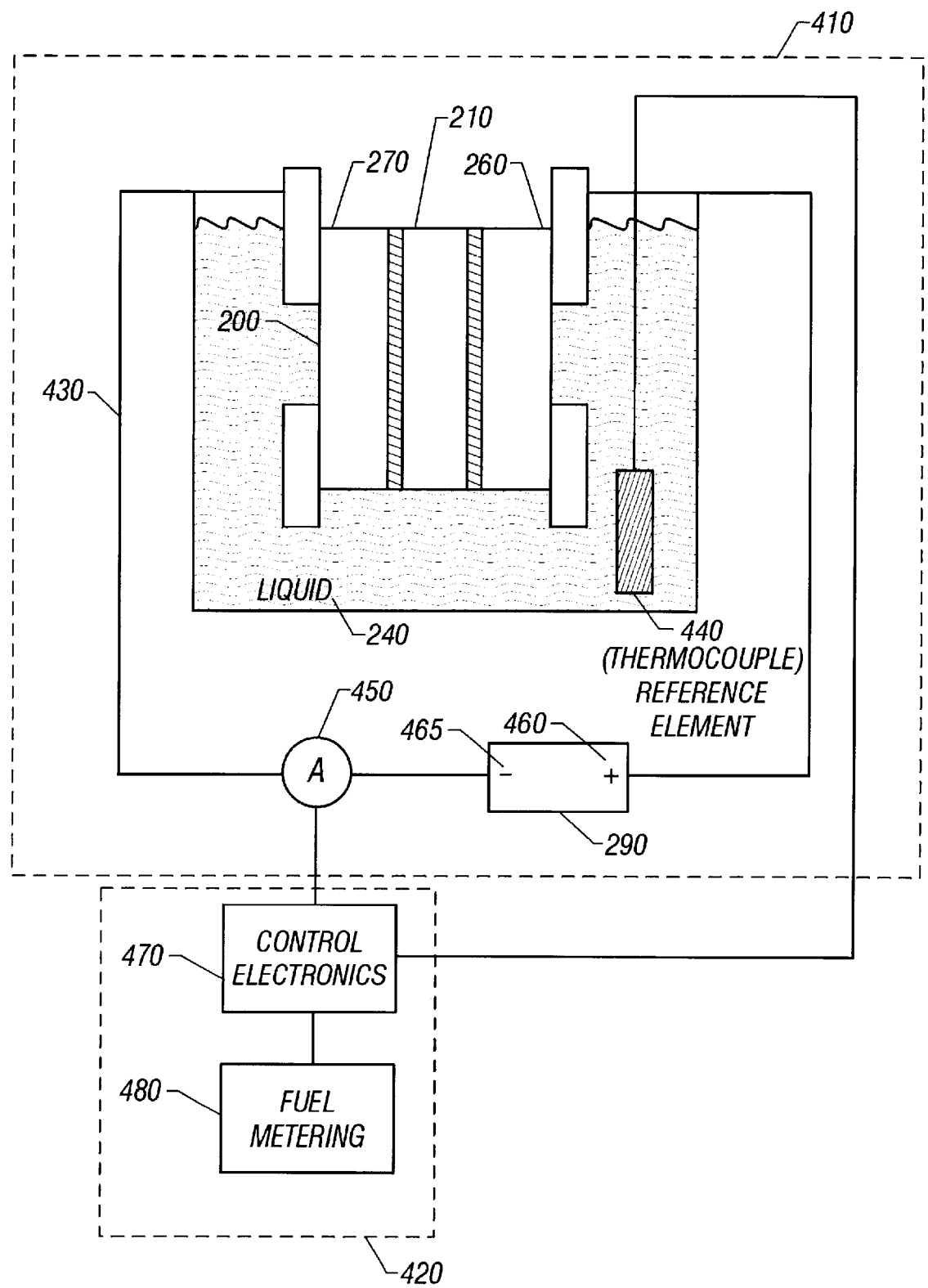
FIG. 4B is a schematic of a single sensor element implementation of the concentration sensor device.

FIGS. 4A–4B illustrate a single sensor element embodiment. A concentration sensor device 410 is connected to a fuel metering control system 420. The concentration sensor device 410 has a sensor element 200 connected to a sensor response circuit 430. The sensor response circuit 430 provides a means to detect a concentration dependent response from the sensor element 200. The sensor response circuit 430 outputs the sensor response and inputs the sensor response into the fuel metering control system 420. A reference element 440 is coupled to the sensor element 200 and to the fuel metering control system 420 as shown in FIG. 4A.

In the preferred embodiment, as shown in FIG. 4B, the sensor element 200 has a membrane electrode assembly 210 with both electrodes 260, 270 immersed in a fuel bath 240. The sensor response circuit 430 includes a constant voltage power supply or a "potentiostat" 290, and a device for detecting sensor response such as an ammeter or an alternative current measuring circuit 450. The sensor element 200 is connected to the constant voltage power supply 290, wherein the anode 260 is connected to the positive terminal 460 of the power supply 290 and the cathode 270 is connected to the negative terminal 465 of the power supply 290.

An ammeter is a current measuring device with a particular configuration. Any other current measuring circuit will also be acceptable, such as a shunt with a voltmeter. The ammeter 450 is connected in series in the path of the sensor response circuit 430, in series with the sensor element 200 and the power supply 290.

The ammeter 450 outputs a current measurement to the control electronics 470 of the fuel metering control system 420. The control electronics 470 uses a pre-stored mathematical relation or a lookup table to determine the closest methanol concentration corresponding to the measured current.

The methanol concentration verses measured current relationship is typically temperature dependent. Temperature variations are compensated using a reference element 440, e.g. a thermocouple. The thermocouple is positioned within the fuel bath 240 to measure the temperature of the circulating fuel and make appropriate compensation. The output of the thermocouple is connected to the control electronics 470 of the fuel metering control system 420 to provide correction information. Hence, the fuel metering control system 420 receives one input from the sensor element 200 via the ammeter 450 and receives a second input from the reference element 440.

Different characteristics indicating different temperatures are pre-stored. The closest characteristic is selected based on the specific thermocouple output. Alternately, a correction factor can be determined. The control electronics 470 then sends information to a fuel delivery device 480, which operates to supply an amount of fuel to keep the methanol concentration at a specified level. The information from the control electronics 470 determines the amount and rate of fuel delivery.

Multi-Sensor Element Implementation

Figure 5A:
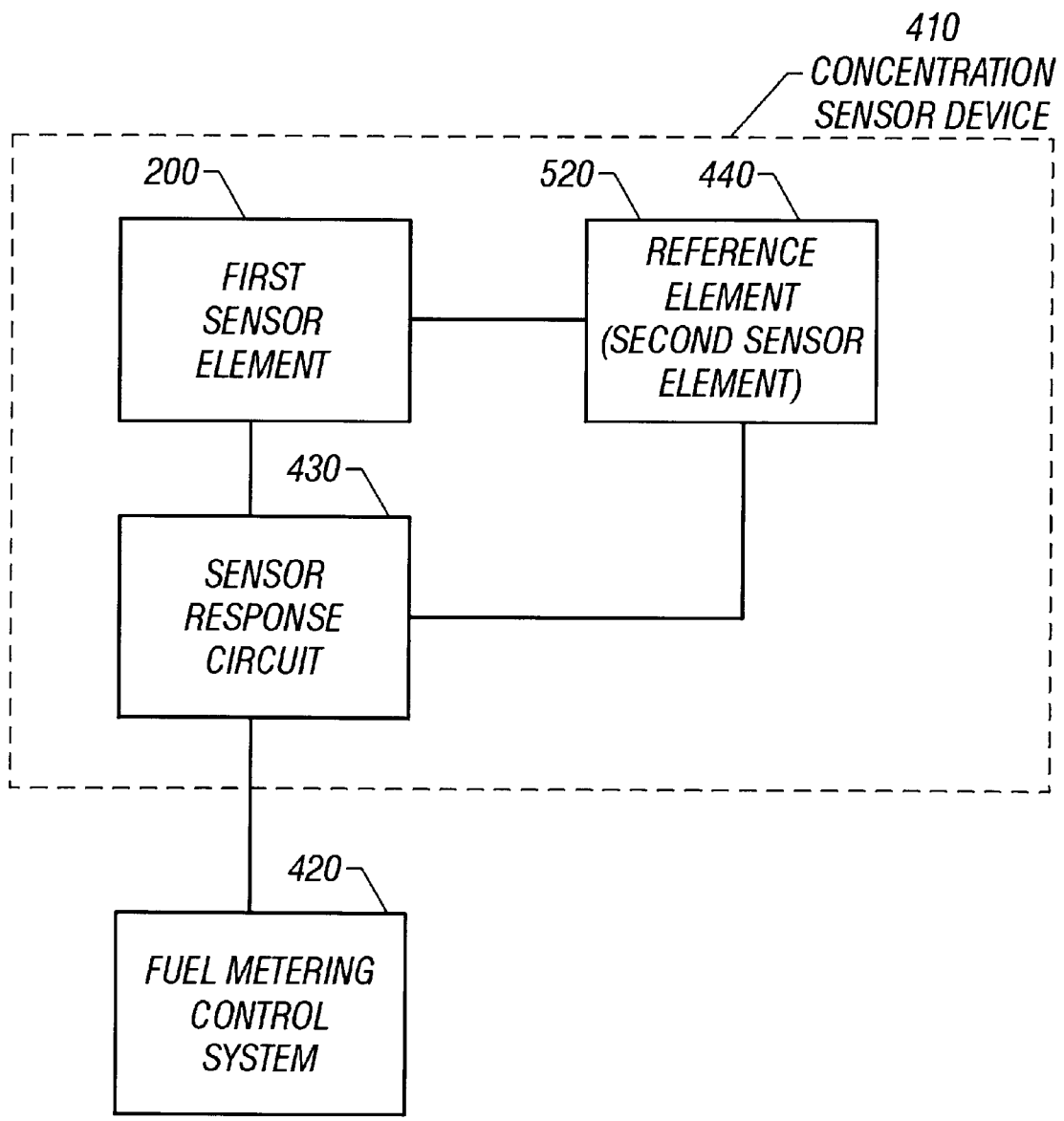
FIG. 5A is a block diagram illustrating a multi-sensor implementation of the concentration sensor device.
Figure 5B:
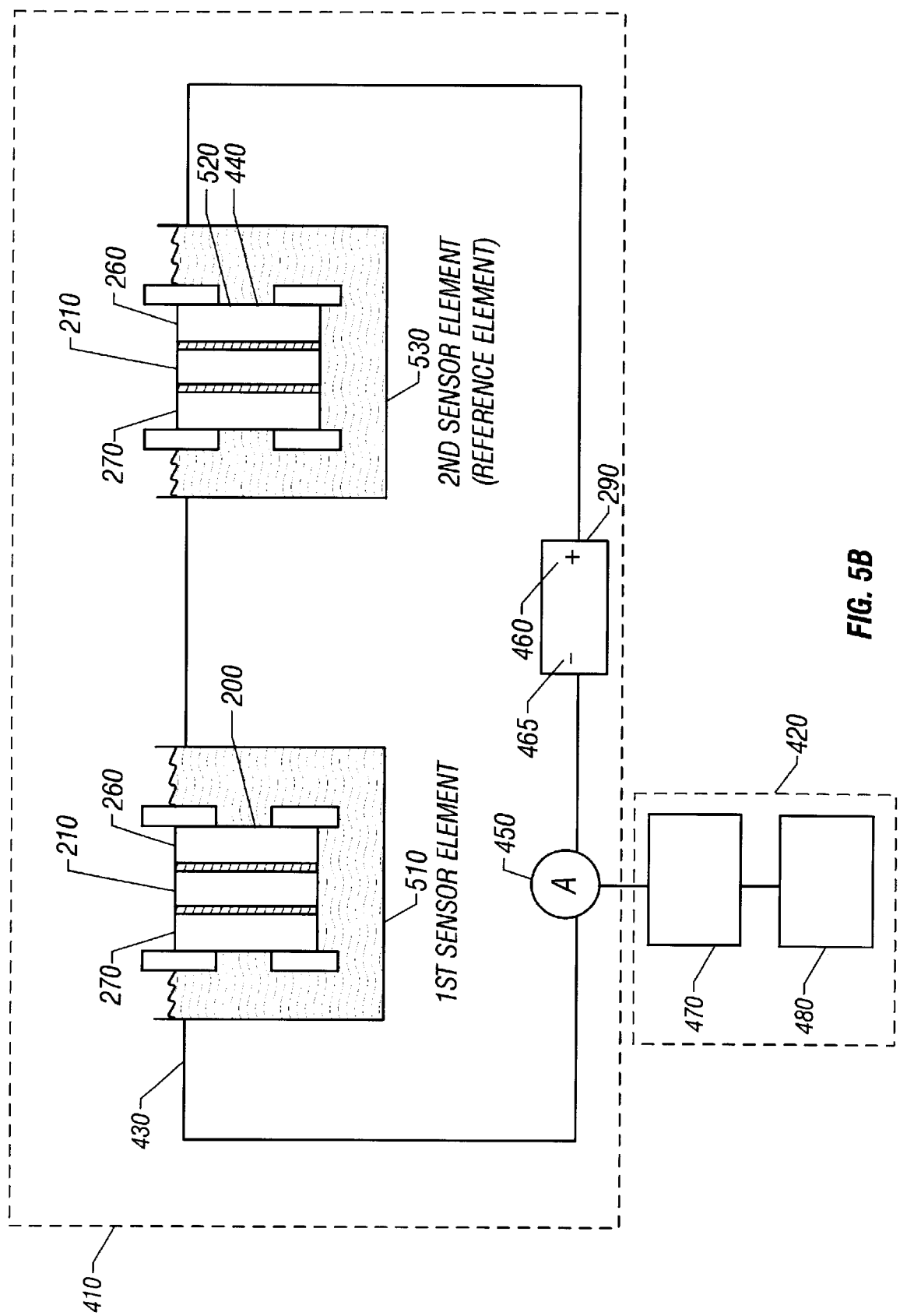
FIG. 5B is a schematic of a multi-sensor implementation of the concentration sensor device.

FIGS. 5A–5B illustrate an alternative embodiment that minimizes the need for calibration and temperature compensation. A first sensor element 200 is placed in an unknown concentration solution bath 510. A second sensor element 520 is maintained in a known concentration solution bath 530 at the same temperature as the unknown concentration bath 510. This known concentration solution bath 530 sets a predetermined reference value for the system. The response of the two sensor elements 200, 520 can be compared and the deviation from the reference can be determined and corrected.

FIG. 5A is a block diagram of the preferred embodiment. A concentration sensor device 410 is connected to a fuel metering control system 420. The concentration sensor device 410 has a first sensor element 200 connected to a second sensor element 520. The second sensor element 520 functions as the reference element 440. Both the first sensor element 200 and the reference element 440 are connected to a sensor response circuit 430. The sensor response circuit 430 provides a means to detect a concentration dependent response from the first sensor element 200 and the second sensor element 520. The sensor response circuit 430 outputs the sensor response and inputs the sensor response into the fuel metering control system 420.

Since the reference element 440 is connected to the sensor element 200 and the sensor response circuit 430, there is no need for a separate reference element to be connected to the fuel metering control system. The second sensor element 520 is a sensor of temperature, therefore there is no need for a thermocouple used in FIGS. 4A–4B.

This embodiment is shown in detail in FIG. 5B. Preferably, both the first sensor element 200 and the reference element 440 are membrane electrode assemblies 210. The first sensor element 200 is in a solution of unknown concentration 510. The reference element 440 is in a solution of known concentration 530. Both the sensor 200 and reference 440 elements are mounted membrane electrode assemblies 210. The anode 260 of the sensor element to is connected to the positive terminal of the constant voltage power supply or "potentiostat" 290. The cathode of sensor element 1 is 270 connected to the negative terminal 465 of the power supply 290.

An ammeter or alternative current measuring circuit 450 is connected in series in the path of the sensor response circuit 430, in series with the constant voltage power supply or "potentiostat" 290, the first sensor element 200, and the reference element 440. An ammeter is a current measuring device with a particular configuration. Any other current measuring circuit will also be acceptable, such as a shunt with a voltmeter.

The ammeter 450 sends the sensor response to the control electronics 470 of the fuel metering control system 420. The fuel metering control system 420 includes the control electronics 470 and fuel delivery device 480 which delivers a controlled amount of fuel to the fuel cell at a controlled metered rate.

Performance Data

Figure 6:
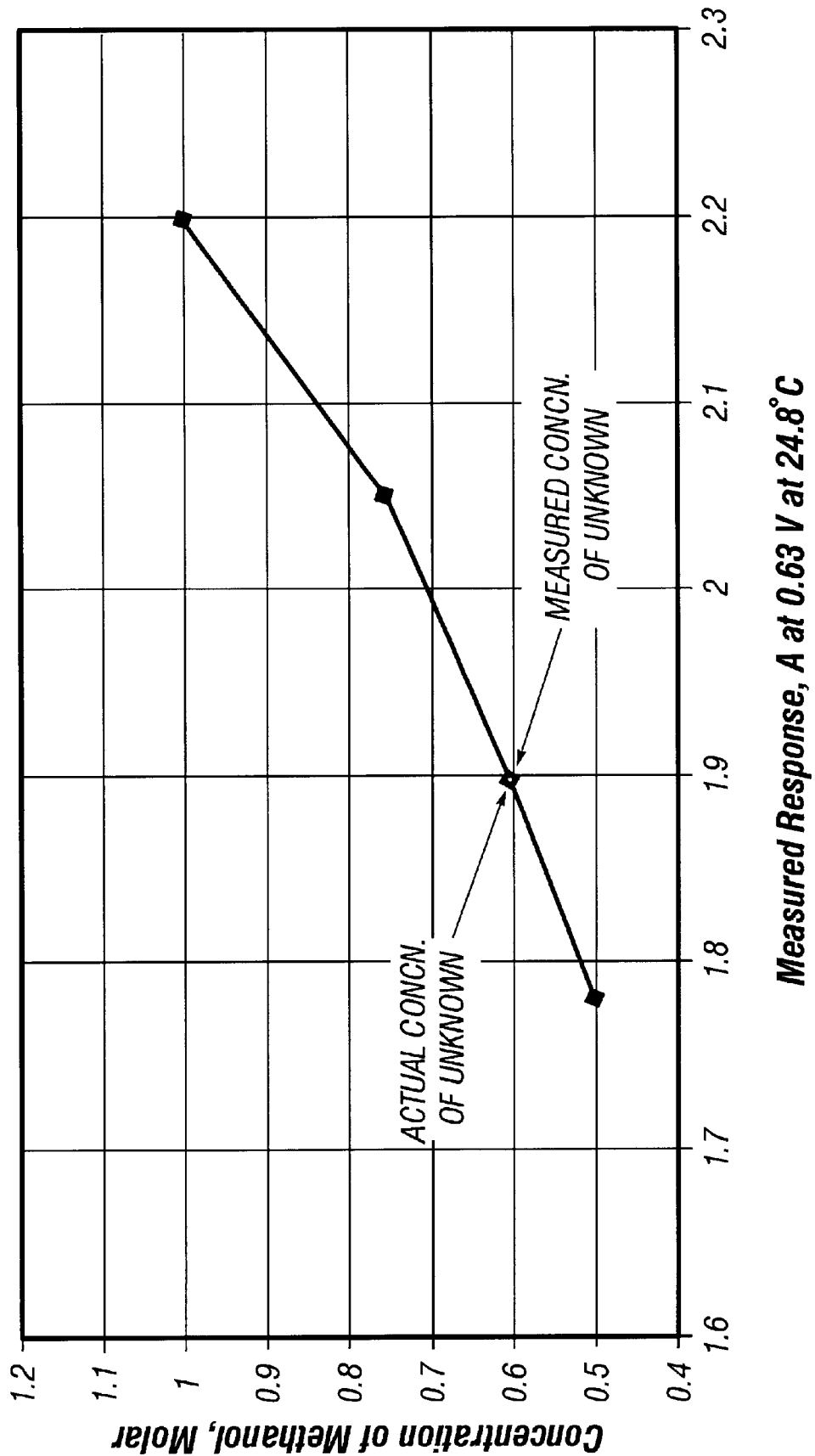
FIG. 6 is a graph illustrating the estimation of concentration of methanol employing the concentration sensor device.

Solutions of known concentration were chosen and the sensor calibration curve established. After this a test solution of known concentration was prepared and its concentration estimated using the sensor response. The agreement with the known value of concentration for the sample was found to be very good. FIG. 6 illustrates this experiment.

Although only a few embodiments have been described in detail above, those having ordinary skill in the art will certainly understand that many modifications are possible in the preferred embodiment without departing from the teachings thereof.

Alternative materials and methods can be used to fabricate the membrane electrode assembly, the membrane support plates and other structures in the sensor element and reference element. Other analyte solutions can be analyzed. One analyte solution used in the preferred embodiment is methanol. Other organic solution can also be processed by the present apparatus. Some of these solutions include oxidizable materials such as formic acid, formaldehyde, dimethoxymethane, trioxane, trimethoxymethane, dimethyl carbonate, acetic acid, ethanol, acetaldehyde, and oxygenated hydrocarbons such as ethers and furans.

All such modifications are intended to be encompassed within the following claims.

What is claimed is:

1. A method for detecting a methanol-compound concentration in an aqueous environment, comprising:

using a sensor element probe a liquid analyte solution including methanol to produce a sensor response, said sensor element including an anode, a solid electrolyte membrane and a cathode, wherein said sensor element includes a catalyst which is capable of chemically reacting with methanol;

immersing both the anode and the cathode in the liquid analyte solution;

using an electrical power supply having a positive terminal and a negative terminal to supply power to said sensor element, wherein said positive terminal is connected electrically to said anode and said negative terminal is connected electrically to said cathode; and connecting an analyte concentration sensing device to said sensor element for detecting a response of said sensor element to said analyte, said device being connected electrically to said sensor element and said power supply and detecting an amount of current consumed thereby.

2. The method as in claim 1, wherein said sensor response has a magnitude that is proportional to a concentration of said methanol solution.

3. The method as in claim 1, wherein said electrical power supply delivers a constant voltage.

4. The method as in claim 1, wherein said electrical power supply delivers a voltage sufficient to supply a threshold high anode potential for said sensor element.

5. The method as in claim 4, wherein said threshold potential is in excess of 0.3 volts.

6. The method as in claim 1, wherein said analyte concentration sensing device includes an ammeter or any other current measuring circuit.

7. The method as in claim 1, further comprising mounting said sensor element in supports which have two members for mounting such that one member is in contact with the anode and that the other member is in contact with the cathode.

8. The method as in claim 7, wherein said supports function to expose the sensor element to the analyte solution.

9. The method as in claim 8, wherein said supports are plates with at least one aperture.

10. The method as in claim 7, further comprising using said supports as current collectors.

11. The method as in claim 10, wherein said supports are made of graphite or graphite-bonded resins, conductive or metallized plastics, coated-metals, including one of titanium with platinum, gold, or titanium nitride, or noble metal coated stainless steel.

12. The method as in claim 1, further comprising providing and operating a fuel metering control system to supply an amount of analyte to keep the analyte concentration at a specified level.

13. The method as in claim 12, further comprising using a pre-stored mathematical relation or a lookup table in operation of said fuel metering control system to determine the closest analyte concentration corresponding to said sensor response.

14. The method as in claim 12, further comprising providing and using a reference element to compensate for temperature dependence of said sensor response.

15. The method as in claim 14, wherein said reference element includes a thermocouple.

16. The method as in claim 15, wherein said thermocouple is positioned within said analyte solution and is coupled to said fuel metering control system.

17. A method for detecting an analyte concentration in an aqueous environment, comprising:

using a sensor element to contact an analyte solution including methanol to produce a sensor response, wherein said sensor element includes a first anode, a first solid electrolyte membrane and a first cathode;

immersing both said first anode and said first cathode in the analyte solution at a certain temperature;

using a reference element to produce a reference response indicating a temperature, wherein said reference element is connected electrically to said first sensor element, said reference element including a second anode, a second solid electrolyte membrane and a second cathode;

immersing both said second anode and said second cathode in a reference solution at the same temperature as said analyte solution;

connecting a power supply to said sensor element and said reference element; and using an analyte concentration sensing device to detect a response of said sensor element to said methanol, said device being connected electrically to said sensor element, said reference element and said power supply.

18. The method as in claim 17, wherein said sensor response has a magnitude that is proportional to a concentration of said analyte solution.

19. The method as in claim 17, wherein said power supply delivers a constant voltage.

20. The method as in claim 17, wherein said power supply delivers a voltage sufficient to supply a threshold high anode potential for said sensor element.

21. The method as in claim 20, wherein said threshold potential is in excess of 0.3 volts.

22. The method as in claim 17, wherein said analyte concentration sensing device includes an ammeter or any other current measuring circuit.

23. The method as in claim 22, wherein said ammeter or other current measuring circuit is connected electrically in series with said first sensor element, said second reference element, and said power supply.

24. The method as in claim 17, further comprising mounting said sensor element in supports, said supports having two members mounted such that one member is in contact with the first anode and that the other member is in contact with the first cathode.

25. The method as in claim 17, further comprising mounting said reference element in supports, said supports having two members mounted such that one member is in contact with the second anode and that the other member is in contact with the second cathode.

26. The method as in claim 17, further comprising providing a fuel metering control system to supply an amount of analyte to keep the analyte concentration at a specified level.

27. The method as in claim 26, wherein said fuel metering control system uses one of a pre-stored mathematical relation or a lookup table to determine the closest analyte concentration corresponding to said sensor response.

28. The method as in claim 1, wherein said analyte solution includes methanol including oxidizable materials including one of formic acid, formaldehyde, dimethoxymethane, trioxane, trimethoxymethane, dimethyl carbonate, acetic acids ethanol, acetaldehyde, or oxygenated hydrocarbons.

29. The method as in claim 17, wherein said analyte solution includes methanol and further includes oxidizable materials such as formic acid, formaldehyde, dimethoxymethane, trioxane, trimethoxymethane, dimethyl carbonate, acetic acid, ethanol, acetaldehyde, or oxygenated hydrocarbons.

30. The method as in claim 17, wherein said reference solution includes methanol and further includes oxidizable materials such as formic acid, formaldehyde, dimethoxymethane, trioxane, trimethoxymethane, dimethyl carbonate, acetic acid, ethanol, acetaldehyde, or oxygenated hydrocarbons.

31. The method as in claim 17 wherein said sensor element includes a catalyst material thereon which is effective to operate in breaking down said analyte.

* * * * *